(12) United States Patent
Hecht

(10) Patent No.: US 9,541,566 B2
(45) Date of Patent: Jan. 10, 2017

(54) ACCOMMODATING MAGAZINE

(71) Applicant: GLP Systems GmbH, Hamburg (DE)

(72) Inventor: Robert Hecht, Seehausen (DE)

(73) Assignee: GLP Systems GmbH, Hamburg (DE)

( * ) Notice: Subject to any disclaimer, the term of this patent is extended or adjusted under 35 U.S.C. 154(b) by 241 days.

(21) Appl. No.: 14/374,587

(22) PCT Filed: Jan. 18, 2013

(86) PCT No.: PCT/EP2013/050933
§ 371 (c)(1),
(2) Date: Jul. 25, 2014

(87) PCT Pub. No.: WO2013/110554
PCT Pub. Date: Aug. 1, 2013

(65) Prior Publication Data
US 2015/0075298 A1    Mar. 19, 2015

(30) Foreign Application Priority Data

Jan. 27, 2012 (EP) .................................. 12152830

(51) Int. Cl.
| | | |
|---|---|---|
| *G01N 35/04* | (2006.01) | |
| *G01N 35/02* | (2006.01) | |
| *G01N 1/28* | (2006.01) | |

(52) U.S. Cl.
CPC ............. *G01N 35/026* (2013.01); *G01N 1/28* (2013.01); *G01N 35/02* (2013.01); *G01N 35/04* (2013.01); *G01N 2035/0491* (2013.01); *G01N 2035/0493* (2013.01); *G01N 2035/0498* (2013.01)

(58) Field of Classification Search
CPC ............. G01N 2035/0498; G01N 2035/00752; G01N 2035/00762; G01N 2035/0493; G01N 2035/0494
See application file for complete search history.

(56) References Cited

U.S. PATENT DOCUMENTS

| | | | | |
|---|---|---|---|---|
| 3,955,179 A | * | 5/1976 | Planke | B07C 5/126 209/525 |
| 4,553,217 A | * | 11/1985 | Daudt | B07C 5/126 209/525 |
| 5,038,023 A | * | 8/1991 | Saliga | B60R 25/24 235/383 |
| 5,266,810 A | * | 11/1993 | Murphy | G01V 8/20 250/222.1 |

(Continued)

FOREIGN PATENT DOCUMENTS

DE        19912211        12/2001

*Primary Examiner* — David A Rogers
(74) *Attorney, Agent, or Firm* — Sand & Sebolt

(57) ABSTRACT

An accommodating magazine for accommodating a plurality of sample carriers in a sample holder for use in an input or output area of an automated sample handling device. The magazine comprises a magazine panel, a detection device for detecting whether the panel is filled with sample holders or sample carriers during movement of the panel between a loading position and a ready position. The detection device includes at least one contactless detector for detecting the presence of objects in a sensor area, a path sensor, which detects a displacement path or current position of the panel during displacement of the panel between the loading and ready positions; and an evaluating unit in which the detector data and the path sensor data are merged and are evaluated.

17 Claims, 3 Drawing Sheets

(56) References Cited

U.S. PATENT DOCUMENTS

| | | | | |
|---|---|---|---|---|
| 5,448,078 A * | 9/1995 | Nakazawa | G06K 7/10861 | 250/559.24 |
| 5,923,428 A | 7/1999 | Woodworth | | |
| 6,255,614 B1 | 7/2001 | Yamakawa | | |
| 7,081,713 B2 * | 7/2006 | Jurs | F16P 3/14 | 250/221 |
| 7,126,144 B2 * | 10/2006 | De Coi | G01B 11/024 | 250/221 |
| 8,867,045 B2 * | 10/2014 | Piana | G01V 8/20 | 356/614 |
| 2008/0078143 A1 * | 4/2008 | Uehara | G07D 1/02 | 53/212 |
| 2009/0166227 A1 * | 7/2009 | Imai | G07D 1/02 | 206/0.81 |
| 2010/0039513 A1 * | 2/2010 | Glickman | G06K 9/00 | 348/143 |
| 2010/0080442 A1 * | 4/2010 | Sones | G01N 21/9036 | 382/143 |
| 2011/0115610 A1 * | 5/2011 | Hughes | B01L 9/00 | 340/10.1 |
| 2011/0141265 A1 * | 6/2011 | Holtkamp | G01J 5/0003 | 348/86 |
| 2013/0076898 A1 * | 3/2013 | Philippe | H04N 7/18 | 348/143 |
| 2013/0082581 A1 * | 4/2013 | Bufalini | G07F 11/62 | 312/209 |
| 2013/0092187 A1 * | 4/2013 | Lim | B08B 3/00 | 134/8 |
| 2013/0242085 A1 * | 9/2013 | Gut | G01N 21/958 | 348/127 |
| 2013/0325175 A1 * | 12/2013 | Rahilly | G07F 11/005 | 700/237 |
| 2015/0179016 A1 * | 6/2015 | Rahilly | E05B 65/46 | 221/154 |

* cited by examiner

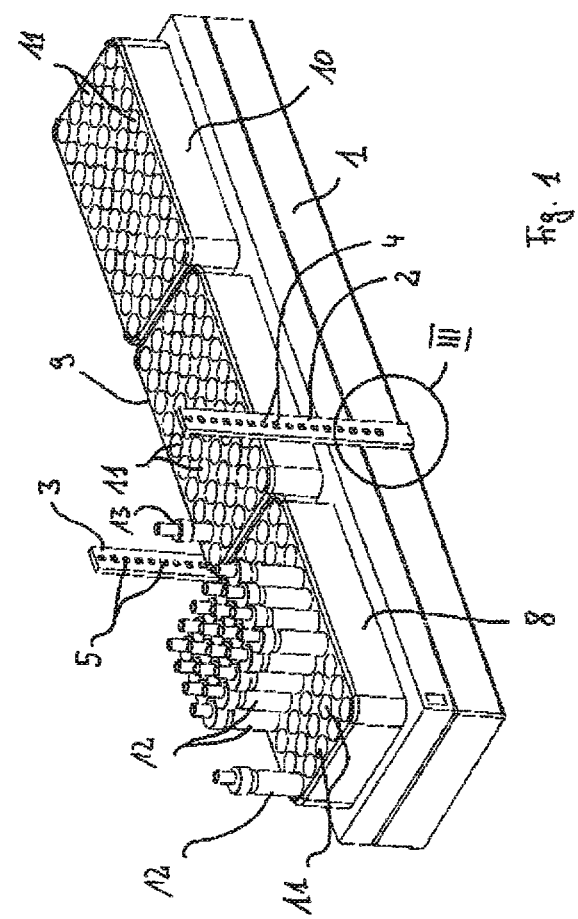

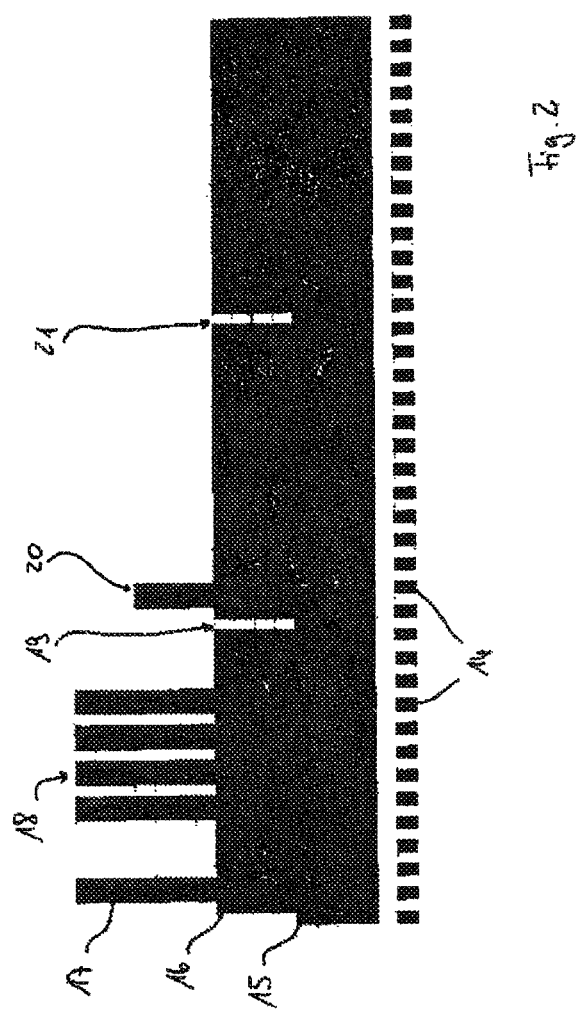

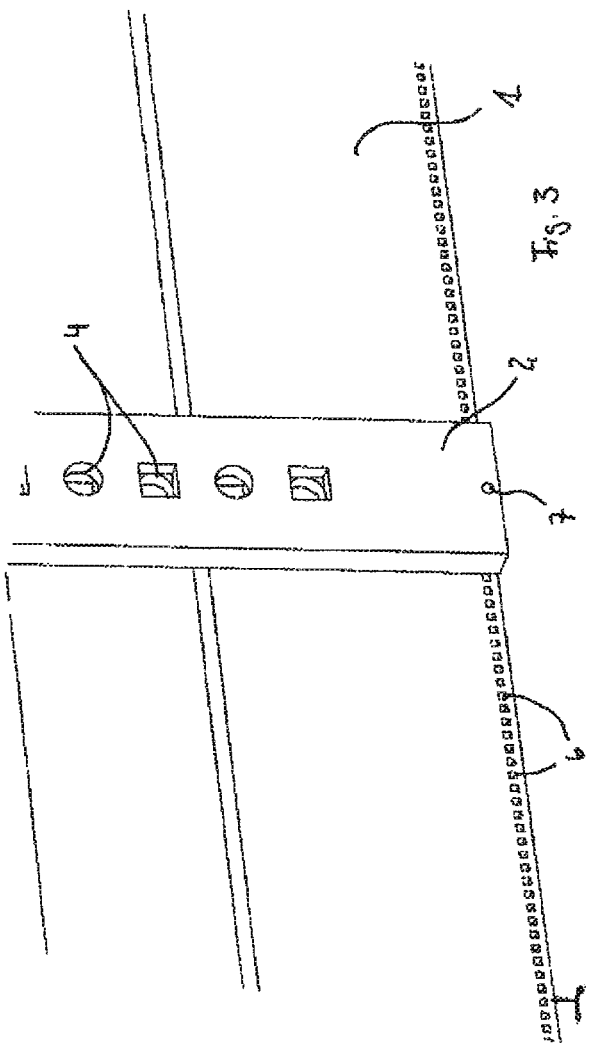

ACCOMMODATING MAGAZINE

TECHNICAL FIELD

The invention relates to an accommodating magazine for accommodating a plurality of cylindrical sample carriers that are elongated along a longitudinal axis and are essentially cylindrical. The invention also relates to a method for monitoring a magazine panel according to claim 8 for the presence of sample carriers and/or sample holders thereon.

PRIOR ART

It is known in diagnostic medical laboratories in particular, but also in other laboratories and facilities accustomed to handling samples, that samples filled into sample carriers can be treated and moved in an automated fashion over at least some parts of a process sequence.

For example, there is a known sample sorter, which is described in DE 199 12 211 A1, with which samples in tubular sample carriers, e.g., samples of body fluids from patients, can be sorted in an automated process. The sample sorter disclosed in that citation comprises an intake area and a discharge area, such that panel-type pull-out tables that are present in both areas can be loaded with sample holders, also referred to there as racks, these sample holders being designed to hold the sample carriers. For manual loading of the pull-out tables with sample holders and/or manual loading of the sample holders on the pull-out tables with sample holders, the pull-out table may be pulled out into a loading position in which manual loading is possible. The pull-out table is next moved into a ready position, in which the individual sample carriers are detected with a robot gripper and can be sorted.

Such automated sorting reduces not only the personnel costs in a corresponding laboratory but also reduces the error susceptibility and can accelerate processes. However, corresponding automation systems have not been limited to only a sample sorter manifested in a single device such as that disclosed in DE 199 12 211 A1, but it is also conceivable to position similar holding magazines in automated analysis systems from which an automatic analysis zone receives individual samples and/or where samples that have passed through an automated analysis zone are collected at the end of that zone and stored temporarily prior to manual retrieval.

Holding magazines such as those on the known sample sorter according to DE 199 12 211 A1 in its intake area and/or its discharge area, are typically loaded and/or emptied manually, for which purpose an operator who brings the displaceable magazine panels, which are referred to as pull-out tables in DE 199 12 211 A1, out of the ready position and into the loading position (either lifting them mechanically or moving them by motor drive), to then adjust or retrieve the sample holders accordingly or to retrieve sample carriers from the sample holders remaining on the magazine panel or to place the corresponding sample carriers in them.

This manual loading, like any human intervention, constitutes a source of error. Thus, in the case of a magazine panel to be emptied, for example, an operator may fail to retrieve one or more sample holders or sample carriers and/or sample carriers disposed on sample holders and may move the magazine panel back into the ready position too soon. It is also conceivable, for example, in manual input of the loading of a magazine panel in an area where sample carriers are fed into an automated system, for false entries to be input, certain locations for sample carriers or sample holders to be listed as unoccupied when actually the sample carriers or sample holders are located there and/or vice-versa. All of these may unavoidably result in errors in a subsequent automated sequence, when sample holders to be manipulated cannot be gripped by an automated system if the corresponding positions are listed as "unoccupied" and/or when, in that another sample carrier is set down in positions guided to in a placement area, where sample carriers have inadvertently remained in a position that is presumably not occupied, and this results in a collision or, in the worst case, destruction of the sample carrier and thus, for example, in the case of an automated medical diagnostic system, resulting in contamination of the system with a blood sample, a urine sample or the like, for example, and can thus lead to a shutdown of the system, so that a decontamination can be performed. Conversely, it is also possible for a sample carrier, which is supposed to be placed in a sample holder that is presumably present there, to be set down without the sample holder actually being located there. The sample carrier would not be reliably accommodated in such a case, which here again could lead to an accident or in the worst case to contamination of the system.

Since the fees paid for individual analyses in modern medical laboratory analyses in particular are extremely low, a medical laboratory can operate economically only if it has a high throughput of samples. Failure of an automated analysis system there means particularly high economic damages.

DESCRIPTION OF THE INVENTION

The problems described above are to be counteracted with the present invention by the creation of a simple and reliable detection possibility with which the presence of sample holders and/or sample carriers on the magazine panel can be detected and can be compared with expected values.

This object is achieved with regard to the device by an accommodating magazine for accommodating a plurality of sample carriers in particular essentially cylindrical and elongated along a longitudinal axis, in at least one sample holder equipped to accommodate several such sample carriers for the automated handling of individual sample carriers of such a type, in particular retrieval from and/or insertion into the sample holders, in particular for use in an input region or an output region of an automated sample handling system, wherein the accommodating magazine comprises a magazine panel, which is displaceable essentially horizontally, like a drawer, between a ready position, in which the accommodating magazine is ready for automated handling of the individual sample carriers, and a loading position, in which sampling carriers and/or sample holders can be introduced manually and/or retrieved manually, and the at least one sample holder is and/or can be disposed on said magazine panel, characterized by a load detection device for detecting a load of the magazine panel with sample holder(s) and/or sample carriers in the movement of the magazine panel between the loading position and the ready position. The accommodating magazine comprises at least one detector, which operates without contact for detecting the presence of objects in a sensor region, which is disposed in a path of movement of sample holders and/or sample carriers disposed on the magazine panel, such that it can detect sample holders and/or sample carriers disposed on the magazine panel and passing by its sensor region; a displacement sensor, which detects a displacement and/or a current position of the magazine panel upon displacement of same between the loading position and the ready position, and an evaluation unit in which the data of the detector and of the displacement sensor are combined and evaluated with regard to the presence of at least one sample holder and/or sample carrier in correlation with a certain path position of the displacement. Advantageous refinements of such an accommodating magazine are characterized in that the detector, which operates without contact, is a photoelectric barrier, particularly a transmission photoelectric barrier. Still further the displacement sensor is an incremental sensor, which detects optically or magnetically. The accommodating magazine may have at least two, in particular a plurality of, non-contact detectors disposed vertically one above the other in a detection region, disposed at positions, by which sample holders and sample carriers that are disposed on the magazine panel pass in projection thereof in displacement of the magazine panel. The evaluation unit is equipped for recording a profile of sample carriers and sample holders, which are detected by detectors disposed vertically one above the other, the sample holders and sample carriers being disposed on the magazine panel. Additionally, the evaluation unit is equipped for output of an alarm signal when, in deviation from a predetermined stipulation of a certain position in correlation, a sample holder and/or a sample carrier is detected or is not detected. Another aspect in solving this problem consists of a method for monitoring for the presence of sample carriers and/or sample holders on a magazine panel. The method includes monitoring for the presence of essentially cylindrical sample carriers and/or sample holders that are elongated along a longitudinal axis to accommodate such sample carriers on a magazine panel of an accommodating magazine that is displaceable essentially horizontally, like a drawer, between a ready position and a loading position; for accommodating a plurality of such sample carriers in at least one sample holder, wherein sample holders and/or sample carriers passing by the sensor region in displacement of the magazine panel are detected by means of at least one detector operating without contact for detecting the presence of objects in a sensor region, wherein also, by means of a displacement sensor, the displacement distance of the magazine panel in its displacement is detected and wherein the displacement distance and the detection by the detector are correlated in such a way that a distance position at which the presence of a sample holder and/or sample carrier is detected is linked to the detection signal of the sample holder and/or sample carrier thereby detected, to form a data record. The method is further characterized in that a projection profile of the sample holders and/or sample carriers disposed on the magazine panel is recorded by two or more detectors during displacement of the magazine panel and this result is correlated with the position of the magazine panel detected by the displacement sensor along the displacement distance. Still further, the method is characterized in that a projection profile of the sample holders disposed on the magazine panel is recorded, and on the basis of the geometric dimensions of the projection profile of a known projection of a sample holder and comparison of these dimensions with known dimensions of various types of sample holders that can be disposed on the magazine profile, the type of this sample holder is determined. The projection profile of the sample carriers disposed on the magazine panel is recorded and, on the basis of the geometric dimensions of the projection profile of a recognized projection of a sample carrier and comparison of these dimensions with known dimensions of various types of sample carriers that can be disposed on the magazine panel, the type of this sample carrier is determined. The method is further characterized in that an alarm is output in the unexpected presence and/or absence of a sample holder and/or a sample carrier in comparison with a stipulation.

The essential approach of the present invention consists of mounting at least one detector for detecting the presence of objects in a stationary mount on the accommodating magazine (in particular with respect to the displaceable magazine panel), this detector operates by a non-contact principle and covers with a sensor area the area which is traversed by sample holders and/or sample carriers in displacement of the magazine panel. In addition, a displacement sensor detects a displacement distance and/or a current position of the magazine panel in displacement of same between the loading position and the ready position. The data detected by this sensor combination, i.e., the detector and the displacement sensor, is correlated in an evaluation unit. Thus, with the approach according to the invention, it is possible to draw a conclusion about a position on the magazine panel, where a sample holder and/or sample carrier has been detected by the detector.

The correlation of the data may be performed either directly by merging the data detected by the detector with the values detected by the displacement sensor at the same time to form a tuple, but this may also be accomplished by adding additional parameters, for example, a time value which is predefined by the evaluation unit or a control unit in cycles and is assigned to the respective data of the detector and/or the displacement sensor, such that a correlation is then established between the values and/or data outputs of the detector and the displacement sensor based on identical time values in the evaluation unit.

The detector, which operates by a non-contact method, may be a photoelectric barrier in particular, advantageously a transmissive photoelectric barrier (but a reflective photoelectric barrier is fundamentally also possible). A photoelectric barrier is a particularly simple option for such a detector that can be manufactured inexpensively and in a space-saving manner and can be integrated into the system of the accommodating magazine.

The displacement sensor may be in particular an optically or magnetically detecting incremental sensor. This type of design of the displacement sensor is also an implementation that is inexpensive to implement and can be integrated easily into the accommodating magazine. However, other forms of displacement sensors may be used, such as electric sensors (e.g., potentiometers or absolute value generators). In general it is also possible to integrate the displacement sensor into a drive when the drawer-type magazine panel is moved by a motor drive.

To be able to make a statement in particular with regard to the presence of sample holders as well as with regard to the presence of sample carriers in a single measurement operation or alternatively to be able to make statements about the height of the aforementioned elements, it is advantageous if at least two, but in particular a plurality of non-contact detectors, disposed vertically one above the other, are provided in a detection area. Preferably the detector, which operates without contact, is a photoelectric barrier. In particular when a tight grid of detectors is provided in this way, it is possible to record a profile of sample carriers and/or sample holders disposed on the magazine panel with the help of an evaluation unit equipped accordingly and to use the measured values from these detectors, such that more specific conclusions can be reached regarding the type of loading of the magazine panel. Thus, for example, on the basis of geometric dimensions, certain sample holders can be identified when various sample holders that can be used on the magazine panel have different geometric dimensions in the direction of the displacement of the magazine panel or in the vertical direction. It is also fundamentally possible to detect sample carriers of different dimensions and also possibly to draw inferences regarding certain samples when they are typically to be found in sample carriers of certain dimensions.

Sample carriers, such as those used in particular in medical analytical laboratories and diagnostic laboratories, are typically cylindrical holding tubes, in particular those made of plastic. These extend with their longitudinal axis vertically in corresponding sample holders, so that with a grid that is preferably provided according to the advantageous refinement described here, said grid consisting of a plurality of detectors disposed vertically one above the other, for example, their length can be detected, but perhaps also their width can be detected, if the widths differ. It is also possible for several rows of detectors that are disposed one above the other to also be disposed side by side to obtain an even denser sensor image.

It is fundamentally possible to issue an alarm by stipulating a certain loading of the magazine panel with sample holders and/or sample carriers, for example, in the case of a load which actually exists but deviates from that found by means of the sensor system according to the invention, so that an operator can monitor the load status of the accommodating magazine and optionally adjust it and/or notify the system of the correct load. Collisions or other malfunctions of an automated system into which the accommodating magazine according to the invention is integrated can be reliably prevented in this way.

Even if the approach according to the invention cannot lead to triggering of detection with regard to an essentially horizontal direction running across the direction of displacement of the magazine panel, likewise only a projection is detected, it nevertheless creates a particularly simple additional control method, which is sufficient for practical application and helps to detect errors with simple means and to thus prevent the malfunctions that occur subsequently and/or subsequent damages in an automated system equipped with this accommodating magazine.

BRIEF DESCRIPTION OF THE DRAWINGS

Additional advantages and features of the invention are derived from the description of an exemplary embodiment on the basis of the accompanying figures, in which:

FIG. 1 shows in a perspective view the essential components of an exemplary embodiment of an accommodating magazine according to the invention;

FIG. 2 shows a measurement profile obtained in the evaluation unit by evaluating the measurement results of the detector, which operates by a non-contact method for detecting the presence of objects in its sensor region, as well as the displacement sensor; and FIG. 3 shows an enlarged detail of the diagram from FIG. 1 in a region labeled as III there.

METHODS OF IMPLEMENTING THE INVENTION

The figures show schematically a few of the essential components of an accommodating magazine according to the invention in one exemplary embodiment. These figures and one exemplary embodiment of a possible implementation of an accommodating magazine according to the invention are described below with reference to the figures.

FIG. 1 shows essential components of an accommodating magazine according to the invention in one possible embodiment variant, showing a magazine panel 1 that can be displaced essentially horizontally like a drawer and a pair of sensor strips 2 and 3, which extend essentially vertically and are opposite one another in the direction essentially perpendicular to the longitudinal extent and the direction of movement of the magazine panel 1, said pair being disposed in a stationary position on a corresponding base of the accommodating magazine. These sensor strips 2, 3, as already indicated, are rigidly connected to the base of the accommodating magazine (not shown in detail here) in a stationary mount. The magazine panel 1 is displaceable essentially horizontally, like a drawer, in relation to this base.

Corresponding elements of a detector configuration, namely a photoelectric barrier configuration in this exemplary embodiment, sit in openings 4 and/or 5 disposed one above the other vertically, these openings being formed in the sensor strips 2, 3 and disposed thusly. Openings 4 and/or 5 of the optical transmitters and an optical receiver and/or an optical transmitter/receiver and a reflector are disposed of the sensor strips 2 and/or 3 and aligned horizontally to one another in pairs. With these elements a height profile of detected objects can be recorded in a manner to be described below.

In a lower section, which is shown in an enlarged scale in FIG. 3, the magazine panel 1 has a plurality of marks 6 disposed equidistantly, each consisting of highly reflective elements, for example, or indentations made in the material of the magazine panel or the like. The sensor strip 2, which covers a region of these marks 6 vertically, has an opening 7 in which a corresponding sensor is disposed, pointing with one detection section in the direction of marks 6 and capable of detecting such markings. A displacement sensor is implemented with this assembly, which detects the marks that have gone by in a relative displacement of the magazine panel 1 with respect to the sensor strip 2, and thus detects a progressive displacement distance of the magazine panel 1.

FIG. 1 shows a total of three sample carriers 8, 9, 10 disposed one after the other on the magazine panel 1. These are accommodating blocks for tubular sample holders that are provided with holding openings 11 and can be placed freely on the magazine panel 1. The sample carriers 8, 9, 10 are loaded with sample holders in various ways in the diagram shown here. Thus, a plurality of sample holders 12 of a first design are disposed on the sample carrier 8, such that in the first row shown at the left in the figure, a single sample holder is disposed only in the rear region, the two following rows of holding openings are free of sample carriers, i.e., they have no load, the four following rows are fully loaded with sample holders 12, and, following that, three additional rows with holding openings are not loaded.

However, a sample holder 13 is disposed on the following sample carrier 9 only in a rear position of the second row with holding openings 11. The sample holder 13 has different dimensions in comparison with the sample holders 12, in particular being shorter in its longitudinal extent, and not protruding as far out of the holding opening 11.

The sample carrier 10 is entirely unloaded.

A distance is left between each of the sample carriers 8, 9 and 10 on the end.

The accommodating magazine, which is shown with essential components in the exemplary embodiment, functions as follows:

If the magazine panel 1 is displaced horizontally in relation to the base, which is not shown in greater detail here, and thus also in relation to the sensor strips 2 and/or 3, for example, moving it out of a loading position in which the sample holders and/or sample carriers can be loaded manually (this loading position may occur, for example, when the magazine panel 1 is shifted completely in the direction shown at the right in FIG. 1 in comparison with the sensor strips 2 and 3) into a ready position (then with complete displacement into the region at the left relative to the sensor strips 2, 3 in FIG. 1), then the detectors disposed in the openings 4 and/or 5 in the sensor strips 2 and/or 3, namely photoelectric barriers here, each detect signals of the objects in their sensor path, namely sample holders 8, 9, 10 and/or sample carriers 12, 13. At the same time, the distance traveled by the magazine panel is ascertained by means of the interaction of sensors disposed in the opening 7 of the sensor strip 2 with the marks 6 applied to the magazine panel, as already described in greater detail above. Since the plurality of sensor elements are disposed one above the other in a vertical direction on the sensor strip 2, 3, different numbers of sensors output signals are issued for different heights of the detected objects. If the objects are shallower, the sensors disposed at a higher level do not output any signal.

The detected signals of the sensors and of the displacement sensor disposed in the openings 4, 5 are correlated with one another and sent to an evaluation unit (not shown in greater detail here), where the signals are combined to form a load profile, such as that illustrated in FIG. 2, for the situation depicted in FIG. 1. This shows the individual signals 14, schematically, in the lower section, which are detected by the sensor, which is disposed in the opening 7, when it detects a mark 6 passing by in its field of detection, such that the diagram shown here does not correspond to actual scale, but instead is merely schematic. In fact, substantially more marks 6 are provided than illustrated by the individual signals 14 here.

The detector analysis and/or the profile in FIG. 2 is/are pointing in the same direction, as indicated for the loading pattern of the magazine panel 1 in FIG. 1 that was evaluated. In other words, the start of the profile curve at the left in FIG. 2 corresponds to the edge region of the magazine panel 1 shown at the left in FIG. 1, and the load disposed thereon with sample holders and sample carriers. FIG. 2 shows, at the far left, labeled as 15, the profile for the front edge of the magazine panel 1. Then the photoelectric barrier configuration, as the detector for the presence of objects, detects the front edge of the first sample holder 8 that points in the direction of profile section 16. Then the photoelectric barrier sensors located at a higher level vertically and disposed on the sensor strips 2 and 3 detect the presence of an object at 17, such that this signal section 17 corresponds to the sample holder 12, which is disposed at the farthest to the left. Next, the profile curve again detects the contour of the sample carrier 8 and proceeds upward again in the region 18, i.e., the photoelectric barrier elements disposed vertically in the sensor strips 2 and 3 detect the four successive rows of sample carriers 12 on the sample holder 8 there with a vertical drop in profile in the respective intermediate spaces.

In section 19 the profile curve drops vertically further, i.e., additional photoelectric barrier sensors, which are disposed at higher levels vertically, and would have responded previously because of the sample carrier 8, do not issue any signal here because the interspaces between the end faces of the sample carrier 8 and the sample carrier 9 are disposed there. The subsequent vertical rise of the profile indicates the presence of the sample holder 9, such that an additional vertical rise in section 20 indicates the presence of the sample carrier 13, with a sample curve for a somewhat different configuration of the sample carrier 13 in comparison with FIG. 1 being shown here in FIG. 2, namely for a somewhat different configuration, instead of being for a sample carrier 13 disposed in the second row with openings 11 in the first row of the sample holder 9, this row being disposed entirely at the left.

In the remaining course, the profile, which is output by the detector unit of photoelectric barriers in the sensor strips 2 and 3 in combination with the displacement characteristic detected by the displacement sensor, follows the actual height profile of the sample holder 9. In another section 21 there is then another vertical slump in the profile, which is attributed to the interspace between the sample holder 9 and the sample holder 10. The subsequent rise in the profile shows the sample holder 10 and its profile, with the linear detected profile curve indicating that the sample holder 10 does not contain any sample carriers.

This profile curve, i.e., this detected profile image, can be further evaluated in the evaluation unit and used for corresponding instructions regarding an automatic loading and unloading of the sample holders, for example, in an input region or an output region of an automatic sample handling system, which may include in particular a robot for detecting and shifting individual sample carriers. Thus, with the profile image recorded here, the control unit first detects that a total of three sample holders are disposed on the magazine panel 1, having sample carriers on the first sample holder 8 and the second sample holder 9 and an additional sample holder 10, which is not loaded with samples. Furthermore, the system can, at any rate, determine the respective position of loaded and unloaded rows having holding openings, said position being located transversely to the direction of displacement of the magazine panel 1, as well as being able to differentiate different types of sample holders 12 and 13, based on the different profile heights, such that these differences are expressed in the profile height of the profile curve 17 shown in FIG. 2 and in the region 18, on the one hand, and in the section 20, on the other hand. This information can now be used accordingly to enable unloaded rows of holding openings on sample carriers to output an alarm signal, for example, when no sample holder is disposed in a section provided for loading and the like.

If the sensor device in the sensor strips 2 and 3 does not merely record a profile, as shown in FIG. 2, but instead at the same time detects a receiver and/or reflector and vice-versa, based on a distance measurement from the respective detected sample carriers, determining in which position in the transverse direction to the direction of displacement of the magazine panel 1 a sample carrier 12, 13 is disposed, which is possible in particular from both lateral edges in the exemplary embodiment shown here when the photoelectric barrier elements are each disposed in the openings 4 and/or 5 in alternation, i.e., each following one transmitter and/or transmitter receiver and vertically above same. It is thus possible to obtain additional information that can be evaluated for more accurate control of the system and to prevent errors.

The exemplary embodiment shown here serves only to illustrate the invention and is not to be regarded as restrictive. 1 [sic]

LIST OF REFERENCE NUMERALS

1 Magazine panel
2 Sensor strip
3 Sensor strip
4 Opening

5 Opening
6 Mark
7 Opening
8 Sample carrier
9 Sample carrier
10 Sample carrier
11 Holding opening
12 Sample holder
13 Sample holder
14 Single signal
15 Profile
16 Profile section
17 Profile section
18 Region
19 Section
20 Section
21 Section

The invention claimed is:

1. An accommodating magazine for accommodating a plurality of sample carriers in at least one sample holder equipped to accommodate several such sample carriers for the automated handling of individual sample carriers of such a type, wherein the accommodating magazine comprises the following:
   a magazine panel, which is displaceable essentially horizontally, like a drawer, between a ready position, in which the accommodating magazine is ready for automated handling of the individual sample carriers, and a loading position, in which sampling carriers or sample holders is manually introducible or retrievable, and the at least one sample holder is or can be disposed on said magazine panel, characterized by a load detection device for detecting a load of the magazine panel with sample holder(s) or sample carriers in the movement of the magazine panel between the loading position and the ready position, comprising the following components:
   a) at least one detector, which operates without contact for detecting the presence of objects in a sensor region, which is disposed in a path of movement of sample holders or sample carriers disposed on the magazine panel, such that the detector detects sample holders or sample carriers disposed on the magazine panel and passing by its sensor region;
   b) a displacement sensor, which detects a displacement or a current position of the magazine panel upon displacement of same between the loading position and the ready position, and
   c) an evaluation unit, in which the data of the detector and of the displacement sensor are combined and evaluated with regard to the presence of at least one sample holder or sample carrier in correlation with a certain path position of the displacement; wherein the evaluation unit is equipped for recording a height profile of sample carriers and sample holders which are detected by detectors disposed vertically one above the other, the sample holders and sample carriers being disposed on the magazine panel.

2. The accommodating magazine according to claim 1, wherein the detector, which operates without contact, is a photoelectric barrier.

3. The accommodating magazine according to claim 2, wherein the detector, which operates without contact, is a transmission photoelectric barrier.

4. The accommodating magazine according to claim 1, wherein the displacement sensor is an incremental sensor.

5. The accommodating magazine according to claim 4, wherein the displacement sensor detects optically or magnetically.

6. The accommodating magazine according to claim 1, wherein the accommodating magazine has at least two non-contact detectors disposed vertically one above the other in a detection region, disposed at positions, by which sample holders and sample carriers that are disposed on the magazine panel pass in projection thereof in displacement of the magazine panel.

7. The accommodating magazine according to claim 6, wherein the accommodating magazine has a plurality of, non-contact detectors disposed vertically one above the other in the detection region.

8. The accommodating magazine according to claim 1, wherein the evaluation unit is equipped for output of an alarm signal when, in deviation from a predetermined stipulation of a certain position in correlation, a sample holder or a sample carrier is detected or is not detected.

9. The accommodating magazine according to claim 1, wherein the sample carriers are cylindrical and elongated along a longitudinal axis.

10. The accommodating magazine according to claim 1, wherein the at least one sample holder is equipped to accommodate several such sample carriers for the automated retrieval from or insertion into the sample holders.

11. The accommodating magazine as defined in claim 1, wherein the magazine is for use in an input region or an output region of an automated sample handling system.

12. A method for monitoring for the presence of essentially cylindrical sample carriers or sample holders that are elongated along a longitudinal axis to accommodate such sample carriers on a magazine panel of an accommodating magazine that is displaceable essentially horizontally, like a drawer, between a ready position and a loading position, for accommodating a plurality of such sample carriers in at least one sample holder, wherein sample holders or sample carriers passing by the sensor region in displacement of the magazine panel are detected by means of at least one detector operating without contact for detecting the presence and height of objects in a sensor region, wherein also, by means of a displacement sensor, the displacement distance of the magazine panel in its displacement is detected and wherein the displacement distance and the detection by the detector are correlated in such a way that a distance position at which the presence of a sample holder or sample carrier is detected is linked to the detection signal of the sample holder or sample carrier thereby detected, to form a data record.

13. The method according to claim 12, wherein a projection profile of the sample holders or sample carriers disposed on the magazine panel is recorded by two or more detectors during displacement of the magazine panel and this result is correlated with the position of the magazine panel detected by the displacement sensor along the displacement distance.

14. The method according to claim 13, wherein a projection profile of the sample holders disposed on the magazine panel is recorded, and on the basis of the geometric dimensions of the projection profile of a known projection of a sample holder and comparison of these dimensions with known dimensions of various types of sample holders that are disposable on the magazine profile, the type of this sample holder is determined.

15. The method according to claim 13, wherein a projection profile of the sample carriers disposed on the magazine panel is recorded and, on the basis of the geometric dimensions of the projection profile of a recognized projection of a sample carrier and comparison of these dimensions with known dimensions of various types of sample carriers that are disposable on the magazine panel, the type of this sample carrier is determined.

16. The method according to claim 12, wherein an alarm is output in the unexpected presence or absence of a sample holder or a sample carrier in comparison with a stipulation.

17. An accommodating magazine for accommodating a plurality of sample carriers in at least one sample holder equipped to accommodate several such sample carriers for the automated handling of individual sample carriers of such a type, wherein the accommodating magazine comprises the following:

a magazine panel, which is displaceable essentially horizontally, like a drawer, between a ready position, in which the accommodating magazine is ready for automated handling of the individual sample carriers, and a loading position, in which sampling carriers or sample holders is manually introducible or retrievable, and the at least one sample holder is or can be disposed on said magazine panel, characterized by a load detection device for detecting a load of the magazine panel with sample holder(s) or sample carriers in the movement of the magazine panel between the loading position and the ready position, comprising the following components:

a) at least one detector, which operates without contact for detecting the presence of objects in a sensor region, which is disposed in a path of movement of sample holders or sample carriers disposed on the magazine panel, such that the detector detects sample holders or sample carriers disposed on the magazine panel and passing by its sensor region;

b) a displacement sensor, which detects a displacement or a current position of the magazine panel upon displacement of same between the loading position and the ready position, and c) an evaluation unit, in which the data of the detector and of the displacement sensor are combined and evaluated with regard to the presence of at least one sample holder or sample carrier in correlation with a certain path position of the displacement; and wherein the sample holders contain receptacles to receive individual sample carriers arranged in vertical lines and columns.

* * * * *